US011006671B2

(12) United States Patent
Li et al.

(10) Patent No.: US 11,006,671 B2
(45) Date of Patent: May 18, 2021

(54) ATOMIZING DEVICE, SMOKING ARTICLE HAVING SAME, AND CONTROL METHOD OF ATOMIZING DEVICE

(71) Applicant: Shenzhen First Union Technology Co., Ltd., Shenzhen (CN)

(72) Inventors: Yonghai Li, Shenzhen (CN); Zhongli Xu, Shenzhen (CN); Huiyong Yan, Shenzhen (CN); Yuqin Li, Shenzhen (CN)

(73) Assignee: Shenzhen First Union Technology Co., Ltd., Guangdong (CN)

( * ) Notice: Subject to any disclaimer, the term of this patent is extended or adjusted under 35 U.S.C. 154(b) by 381 days.

(21) Appl. No.: 15/984,352

(22) Filed: May 19, 2018

(65) Prior Publication Data

US 2018/0332895 A1 Nov. 22, 2018

(30) Foreign Application Priority Data

May 19, 2017 (CN) .......................... 201710357952.2

(51) Int. Cl.
*A24F 11/00* (2006.01)
*A24F 47/00* (2020.01)
(Continued)

(52) U.S. Cl.
CPC ............ *A24F 47/008* (2013.01); *A24F 47/00* (2013.01); *A61M 11/042* (2014.02);
(Continued)

(58) Field of Classification Search
CPC ...... A24F 47/008; A24F 40/48; A24F 40/485; A61M 15/0091
(Continued)

(56) References Cited

U.S. PATENT DOCUMENTS

2015/0114407 A1* 4/2015 Duncan ................... A24F 40/53
131/329
2015/0245654 A1* 9/2015 Memari .................... H02J 7/35
141/2

(Continued)

FOREIGN PATENT DOCUMENTS

EP 0 893 071 A1 1/1999
GB 2 533 652 A 6/2016
(Continued)

*Primary Examiner* — Abdullah A Riyami
*Assistant Examiner* — Thang H Nguyen
(74) *Attorney, Agent, or Firm* — PROI Intellectual Property US; Klaus Michael Schmid

(57) ABSTRACT

An atomizing device, an electronic cigarette and a control method for the atomizing device are disclosed. The atomizing device includes a liquid storage assembly configured for storing a tobacco liquid, a liquid guiding assembly connected to the liquid storage assembly and configured for guiding the tobacco liquid, and a heating assembly electrically connected to the battery assembly and configured for atomizing the tobacco liquid; and includes a signal transmitter configured for transmitting a detection signal having a first intensity and a signal receiver configured for receiving a detection signal having a second intensity. The electronic cigarette determines the amount of tobacco liquid on a transmission path of the detection signal according to a difference between the first intensity and the second intensity, and controls on/off of the electrical connection between the heating assembly and the battery assembly according to the determined amount of tobacco liquid.

6 Claims, 6 Drawing Sheets

(51) Int. Cl.

| | |
|---|---|
| *A24F 13/00* | (2006.01) |
| *A24F 17/00* | (2006.01) |
| *A24F 25/00* | (2006.01) |
| *A61M 11/04* | (2006.01) |
| *A61M 15/06* | (2006.01) |
| *G01F 23/296* | (2006.01) |
| *G01F 23/292* | (2006.01) |
| *H05B 1/02* | (2006.01) |

(52) U.S. Cl.
CPC ........... *A61M 15/06* (2013.01); *G01F 23/292* (2013.01); *G01F 23/296* (2013.01); *H05B 1/0297* (2013.01); *A61M 2205/3313* (2013.01); *A61M 2205/3375* (2013.01); *A61M 2205/3386* (2013.01); *A61M 2205/8206* (2013.01)

(58) Field of Classification Search
USPC .................................................. 131/328, 329
See application file for complete search history.

(56) References Cited

U.S. PATENT DOCUMENTS

| | | | |
|---|---|---|---|
| 2016/0029698 A1* | 2/2016 | Xiang | A24F 40/51 |
| | | | 131/328 |
| 2016/0227840 A1* | 8/2016 | Xiang | H05B 1/0225 |
| 2017/0048927 A1* | 2/2017 | Murison | H02J 7/00 |
| 2017/0340009 A1* | 11/2017 | Hon | A24F 47/008 |
| 2018/0020725 A1* | 1/2018 | Alarcon | A24F 40/50 |
| | | | 131/329 |
| 2018/0116284 A1* | 5/2018 | Biel | A24F 40/485 |
| 2018/0360114 A1* | 12/2018 | Qiu | A24F 47/008 |
| 2019/0246698 A1* | 8/2019 | Nakano | A24B 15/167 |
| 2021/0008311 A1* | 1/2021 | Bassin | A61M 16/0069 |

FOREIGN PATENT DOCUMENTS

| | | |
|---|---|---|
| WO | 2016/112542 a1 | 7/2016 |
| WO | 2016/187107 A1 | 11/2016 |

\* cited by examiner

ATOMIZING DEVICE, SMOKING ARTICLE HAVING SAME, AND CONTROL METHOD OF ATOMIZING DEVICE

TECHNICAL FIELD

The present disclosure relates to the technical field of electronic cigarettes, and particularly, to an atomizing device, a smoking article having same, and a control method for the atomizing device.

BACKGROUND

Tobacco cigarette, as a hobby product, is loved by many people. However, the tobacco cigarette contains substances such as tar and carbon monoxide, which are harmful to the health of human bodies; especially the tar contains dozens of carcinogenic ingredients. Therefore, the tobacco cigarette greatly impacts the health of human bodies. At present, national governments have gradually regulated that smoking of traditional cigarettes is forbidden in public occasions. However, for smokers craving for tobacco, it is uncomfortable and miserable not to smoke. Therefore, many substitutes for traditional tobacco cigarettes appear on the market, for example, smoking-quitting lozenges, electronic cigarettes, etc.

At present, electronic cigarettes available on the market all employ the heating method implemented through atomizer's heating wires. A tobacco liquid is guided through a liquid guiding material to the heating wire to be atomized into an aerosol. When the tobacco liquid inside the atomizer is to be used up, the system cannot know that the atomizer needs refill of tobacco liquid, as a result, the user will continue using the electronic cigarette. Consequently, the heating wire of the atomizer will suffer drying-burning. Such dry-burning will burn out the liquid guiding material and generate harmful gases, and the harmful gases will directly impact the health of users.

SUMMARY

The technical problem to be solved by the present disclosure is to provide an atomizing device, an electronic cigarette, and a control method for the atomizing device, which can prevent a liquid guiding assembly from dry-burning and thus can protect human bodies against harmful gases generated by the dry-burning.

In order to solve the above technical problem, the present disclosure employs a technical scheme as follows. An atomizing device is provided, which is assembled with a battery assembly to form an electronic cigarette. The atomizing device includes a liquid storage assembly configured for storing a tobacco liquid, a liquid guiding assembly connected to the liquid storage assembly and configured for guiding the tobacco liquid, and a heating assembly electrically connected to the battery assembly and configured for atomizing the tobacco liquid, wherein the atomizing device further includes a signal transmitter and a signal receiver, wherein the signal transmitter is configured for transmitting a detection signal having a first intensity, and the signal receiver is configured for receiving a detection signal having a second intensity; and the electronic cigarette determines the amount of the tobacco liquid on the transmission path of the detection signal according to a difference between the first intensity and the second intensity, and controls the on/off of the electrical connection between the heating assembly and the battery assembly according to the determined amount of tobacco liquid; wherein the signal transmitter is an infrared signal transmitter, and the signal receiver is an infrared signal receiver; or, the signal transmitter is an ultrasonic signal transmitter, and the signal receiver is an ultrasonic signal receiver.

In order to solve the above technical problem, the present disclosure employs another technical scheme as follows. An electronic cigarette is provided, which includes a battery assembly and an atomizing device connected to the battery assembly, wherein the atomizing device includes a liquid storage assembly configured for storing a tobacco liquid, a liquid guiding assembly connected to the liquid storage assembly and configured for guiding the tobacco liquid, and a heating assembly electrically connected to the battery assembly and configured for atomizing the tobacco liquid, wherein the atomizing device further includes a signal transmitter and a signal receiver, wherein the signal transmitter is configured for transmitting a detection signal having a first intensity, and the signal receiver is configured for receiving a detection signal having a second intensity; and the electronic cigarette determines the amount of the tobacco liquid on the transmission path of the detection signal according to a difference between the first intensity and the second intensity, and controls the on/off of the electrical connection between the heating assembly and the battery assembly according to the determined amount of tobacco liquid; wherein the signal transmitter is an infrared signal transmitter, and the signal receiver is an infrared signal receiver; or, the signal transmitter is an ultrasonic signal transmitter, and the signal receiver is an ultrasonic signal receiver.

In order to solve the above technical problem, the present disclosure employs yet another technical scheme as follows. A control method for the atomizing device is provided, wherein the control method includes: transmitting, by the signal transmitter, a detection signal having a first intensity; receiving, by the signal receiver, a detection signal having a second intensity; and determining the amount of the tobacco liquid on the transmission path of the detection signal according to a difference between the first intensity and the second intensity, and controlling the on/off of the electrical connection between the heating assembly of the atomizing device and the battery assembly according to the determined amount of tobacco liquid; wherein the signal transmitter is an infrared signal transmitter, and the signal receiver is an infrared signal receiver; or, the signal transmitter is an ultrasonic signal transmitter, and the signal receiver is an ultrasonic signal receiver.

The present disclosure has the following beneficial effects: different from the prior art, the atomizing device for electronic cigarettes provided by the present disclosure includes a liquid storage assembly configured for storing a tobacco liquid, a liquid guiding assembly connected to the liquid storage assembly and configured for guiding the tobacco liquid, and a heating assembly electrically connected to the battery assembly and configured for atomizing the tobacco liquid; the atomizing device further includes a signal transmitter and a signal receiver, in which the signal transmitter is configured for transmitting a detection signal having a first intensity, and the signal receiver is configured for receiving a detection signal having a second intensity; and the electronic cigarette determines the amount of the tobacco liquid on the transmission path of the detection signal according to a difference between the first intensity and the second intensity, and controls the on/off of the electrical connection between the heating assembly and the battery assembly according to the determined amount of tobacco liquid. According to the above method, the present disclosure can prevent the liquid guiding assembly from suffering dry-burning and thus can protect human bodies against harmful gases generated by the dry-burning.

DETAILED DESCRIPTION

Figure 1:
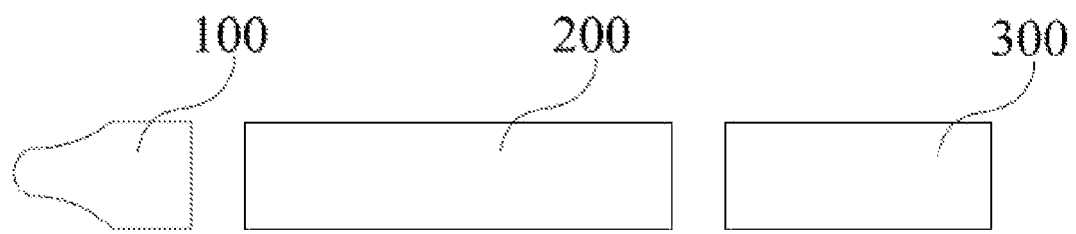
FIG. 1 is a structure diagram of an electronic cigarette according to an embodiment of the present disclosure.

Referring to FIG. 1, which is a structure diagram of an embodiment of an electronic cigarette provided by the present disclosure, the electronic cigarette includes a mouthpiece 100, an atomizing device 200 and a battery assembly 300 that are in connection.

Herein, the atomizing device 200 and the battery assembly 300 can be arranged in a housing; the mouthpiece 100, the atomizing device 200 and the battery assembly 300 can be connected together through threaded connection, magnetic adsorption connection, snap-fit connection and the like to form the electronic cigarette.

In addition, the electronic cigarette can further include a switch, which can be a push button arranged on the housing.

When in work, the electronic cigarette controls, through the switch, the battery assembly 300 to supply power to the atomizing device 200, and the atomizing device transforms the tobacco liquid into an aerosol, which a smoker can inhale through the mouthpiece 100.

The atomizing device 200 of the present disclosure is described below in detail through an embodiment.

Figure 2:
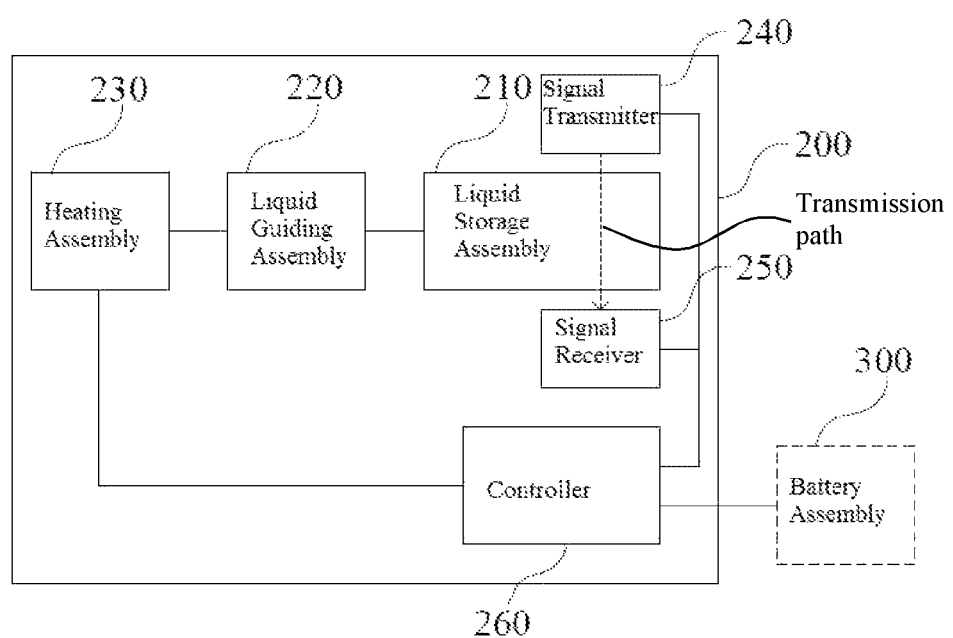
FIG. 2 is a block diagram of an atomizing device according to an embodiment of the present disclosure.

Referring to FIG. 2, which is a structure diagram of an embodiment of an atomizing device provided by the present disclosure, the atomizing device 200 includes:

a liquid storage assembly 210, which is configured for storing a tobacco liquid;

a liquid guiding assembly 220, which is connected to the liquid storage assembly 210 and is configured for guiding out the tobacco liquid in the liquid storage assembly 210; and a heating assembly 230, which is connected to the liquid guiding assembly 220 and the battery assembly 300 and is configured for heating the tobacco liquid in the liquid guiding assembly 220 when the battery assembly 300 supplies power, so as to transform the tobacco liquid into an aerosol for a smoker to inhale.

Optionally, the liquid storage assembly 210 generally is a hollow tubular structure; the hollow tubular structure has a through hole defined on an end part thereof; and the liquid guiding assembly 220 is arranged in the through hole and extends into the inside and outside of the tubular structure so as to guide out the tobacco liquid in the liquid storage assembly 210.

In some variations, the liquid guiding assembly 220 is fiberglass; and the heating assembly 230 is a heating wire.

In the working process of the atomizing device 200, when the tobacco liquid inside the liquid storage assembly 210 is to be used up, the system cannot know that the liquid storage assembly 210 needs refill of tobacco liquid, as a result, the user will continue using the electronic cigarette; consequently, the heating assembly 230 in the atomizing device 200 will suffer dry-burning. Such dry-burning will burn out the liquid guiding assembly 220 and generate harmful gases, and the harmful gases will directly impact the health of users.

In some embodiments, the atomizing device 200 further includes a signal transmitter 240 and a signal receiver 250; the signal transmitter 240 is configured for transmitting a detection signal having a first intensity, and the signal receiver 250 is configured for receiving a detection signal having a second intensity; and the electronic cigarette determines the amount of the tobacco liquid on the transmission path of the detection signal according to a difference between the first intensity and the second intensity, and controls the on/off of the electrical connection between the heating assembly 230 and the battery assembly 300 according to the determined amount of tobacco liquid.

Specifically, in one embodiment, the atomizing device 200 further includes a controller 260; the controller 260 is connected to the signal transmitter 240 and the signal receiver 250 and is configured for acquiring the first intensity and the second intensity and determining the amount of the tobacco liquid on the transmission path of the detection signal according to a difference between the first intensity and the second intensity; and the controller 260 is further connected to the heating assembly 230 and the battery assembly 300 and is configured for controlling the on/off of the electrical connection between the heating assembly 230 and the battery assembly 300 according to the determined amount of tobacco liquid.

In addition, in another embodiment, the controller 250 is not arranged in the atomizing device 200, but arranged in the battery assembly 300; the controller 26 can be an original controller of the battery assembly, and the controller 26 acquires intensity values of the first intensity signal transmitted by the signal transmitter 240 and the second intensity signal received by the signal receiver 250, determines the amount of the tobacco liquid on the transmission path of the detection signal according to a difference between the first intensity and the second intensity, and controls the on/off of the electrical connection between the heating assembly 230 and the battery assembly 300 according to the determined amount of tobacco liquid.

Figure 3:
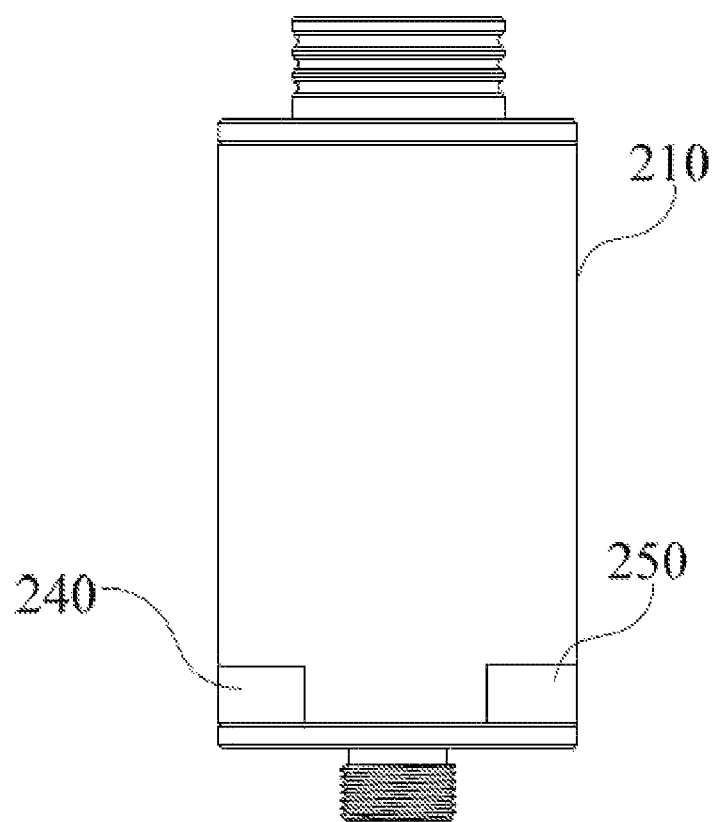
FIG. 3 is a front aspect view of one arrangement for a signal transmitter and a signal receiver in an atomizing device according to an embodiment of the present disclosure.

By reference to FIG. 2 together with FIG. 3, in one specific embodiment, the signal transmitter 240 and the signal receiver 250 are arranged at two opposing sides of a bottom part of the liquid storage assembly 210 respectively.

The signal transmitter 240 is configured for transmitting a detection signal having a first intensity, and the signal receiver 250 is configured for receiving a detection signal having a second intensity; the controller (not shown in FIG. 3) is configured for determining the amount of the tobacco liquid on the transmission path of the detection signal according to a difference between the first intensity and the second intensity, and controlling the on/off of the electrical connection between the heating assembly 230 and the battery assembly 300 according to the determined amount of tobacco liquid.

Herein, the controller is specifically configured for determining that the amount of the tobacco liquid on the transmission path of the detection signal is larger than a preset tobacco liquid amount value when the difference between the first intensity and the second intensity is greater than a preset difference value, and controlling the electrical connection between the heating assembly 230 and the battery assembly 300 to be ON; and determining that the amount of the tobacco liquid on the transmission path of the detection signal is less than a preset tobacco liquid amount value when the difference between the first intensity and the second intensity is less than a preset difference value, and controlling the electrical connection between the heating assembly 230 and the battery assembly 300 to be off.

It is understandable that, during the transmission process of signals, if there is tobacco liquid on the transmission path, the tobacco liquid will absorb the energy of the signal and reduce the intensity of the signal. According to such principle, by detecting the difference between the first intensity and the second intensity, it may be judged whether there is tobacco liquid on the signal path or the amount of the tobacco liquid on the signal path may be calculated.

Specifically, when the difference between the first intensity and the second intensity is greater than a preset difference value, it is determined that there is tobacco liquid on the transmission path of the detection signal or the amount of the tobacco liquid is larger than a preset tobacco liquid amount value, then, it is not needed to add tobacco liquid to the liquid storage assembly and the atomizing device 200 can be normally used; at such time, the heating assembly 230 and the battery assembly 300 are kept in electrical connection. When the difference between the first intensity and the second intensity is less than a preset difference value, it is determined that there is no tobacco liquid on the transmission path of the detection signal or the amount of the tobacco liquid is less than a preset tobacco liquid amount value; at such time, if the heating assembly 230 continues working, the liquid guiding assembly 220 will be burned out and generate harmful gases, and it is needed to add tobacco liquid before normal working; therefore, the heating assembly 230 and the battery assembly 300 are controlled to interrupt the electrical connection therebetween.

Figure 4:
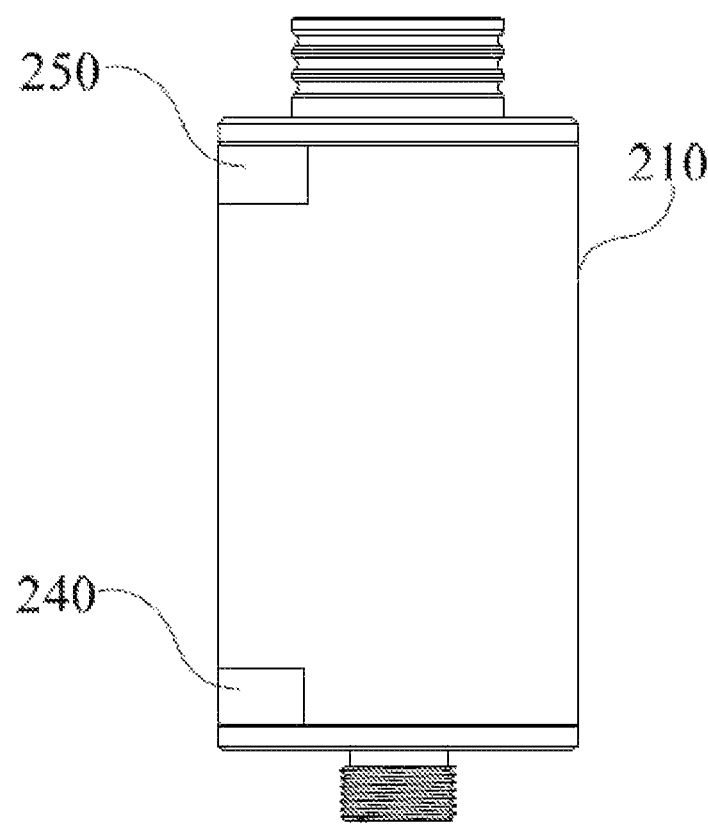
FIG. 4 is a front aspect view of another one arrangement for a signal transmitter and a signal receiver in an atomizing device according to an embodiment of the present disclosure.

By reference to FIG. 2 together with FIG. 4, in another specific embodiment, the signal transmitter 240 and the signal receiver 250 are arranged at a top end and a bottom end of the liquid storage assembly 210 respectively. In some variations, the signal transmitter 240 and the signal receiver 250 are arranged at one same side, or arranged at different sides. No requirement is made here. For example, the signal transmitter 240 may be arranged at the left side of the bottom part, and the signal receiver 250 may be arranged at the right side of the top part.

The signal transmitter 240 is configured for transmitting a detection signal having a first intensity, and the signal receiver 250 is configured for receiving a detection signal having a second intensity; and the controller is configured for determining the amount of the tobacco liquid on the transmission path of the detection signal according to a difference between the first intensity and the second intensity, and controlling the on/off of the electrical connection between the heating assembly 230 and the battery assembly 300 according to the determined amount of tobacco liquid.

Herein, the controller (not shown in FIG. 4) is specifically configured for determining that the amount of the tobacco liquid on the transmission path of the detection signal is larger than a preset tobacco liquid amount value when the difference between the first intensity and the second intensity is greater than a preset difference value, and controlling the electrical connection between the heating assembly 230 and the battery assembly 300 to be ON; and determining that the amount of the tobacco liquid on the transmission path of the detection signal is less than a preset tobacco liquid amount value when the difference between the first intensity and the second intensity is less than a preset difference value, and controlling the electrical connection between the heating assembly 230 and the battery assembly 300 to be off.

It is understandable that, during the transmission process of signals, if there is tobacco liquid on the transmission path, the tobacco liquid will absorb the energy of the signal and reduce the intensity of the signal. According to such principle, by detecting the difference between the first intensity and the second intensity, it can be judged whether there is tobacco liquid on the signal path or the amount of the tobacco liquid on the signal path may be calculated.

Specifically, when the difference between the first intensity and the second intensity is greater than a preset difference value, it is determined that there is tobacco liquid on the transmission path of the detection signal or the amount of the tobacco liquid is larger than a preset tobacco liquid amount value, then, it is not needed to add tobacco liquid to the liquid storage assembly and the atomizing device 200 may be normally used; at such time, the heating assembly 230 and the battery assembly 300 are kept in electrical connection. When the difference between the first intensity and the second intensity is less than a preset difference value, it is determined that there is no tobacco liquid on the transmission path of the detection signal or the amount of the tobacco liquid is less than a preset tobacco liquid amount value; at such time, if the heating assembly 230 continues working, the liquid guiding assembly 220 will be burned out and generate harmful gases, and it is needed to add tobacco liquid before normal working; therefore, the heating assembly 230 and the battery assembly 300 are controlled to interrupt the electrical connection therebetween.

Figure 5:
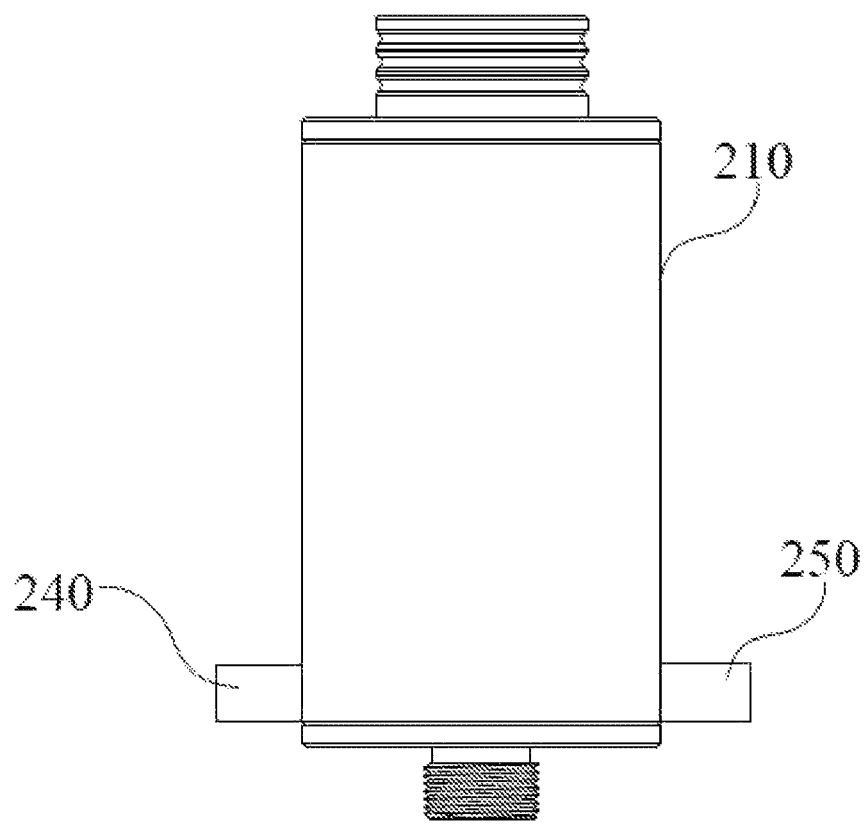
FIG. 5 is a front aspect view of another one arrangement for a signal transmitter and a signal receiver in an atomizing device according to an embodiment of the present disclosure.

In the above two embodiments, both the signal transmitter 240 and the signal receiver 250 are arranged on an inner wall of the liquid storage assembly 210. In other embodiments, the signal transmitter 240 and the signal receiver 250 can also be arranged at two opposing sides on an outer wall of the liquid storage assembly 210, as shown in FIG. 5. It is understandable that the signal transmitter 240 and the signal receiver 250 must be arranged such that the signal path therebetween is the storage space of the tobacco liquid.

It is understandable that the position of the controller 260 can be arranged arbitrarily. No requirement is made in the present embodiment. In addition, in other embodiments, the signal receiver 250 an the controller 260 can also be integrated, that is to say, the signal receiver 250 not only can receive a signal, but also can control the on/off of the electrical connection between the heating assembly 230 and the battery assembly 300 according to the intensity of the signal.

Herein, in the embodiments of FIG. 3 to FIG. 5, the signal transmitter 240 can be an infrared signal transmitter, and the signal receiver 250 can be an infrared signal receiver; in other embodiments, the signal transmitter 240 can be an ultrasonic signal transmitter, and the signal receiver 250 can be an ultrasonic signal receiver.

Different from the prior art, the atomizing device for electronic cigarettes provided by the present disclosure includes a liquid storage assembly configured for storing a tobacco liquid, a liquid guiding assembly connected to the liquid storage assembly and configured for guiding the tobacco liquid, and a heating assembly electrically connected to the battery assembly and configured for atomizing the tobacco liquid; the atomizing device further includes a signal transmitter and a signal receiver, in which the signal transmitter is configured for transmitting a detection signal having a first intensity, and the signal receiver is configured for receiving a detection signal having a second intensity; and the electronic cigarette determines the amount of the tobacco liquid on the transmission path of the detection signal according to a difference between the first intensity and the second intensity, and controls the on/off of the electrical connection between the heating assembly and the battery assembly according to the determined amount of tobacco liquid. According to the above method, the present disclosure can prevent the liquid guiding assembly from suffering dry-burning and thus can protect human bodies against harmful gases generated by the dry-burning.

Figure 6:
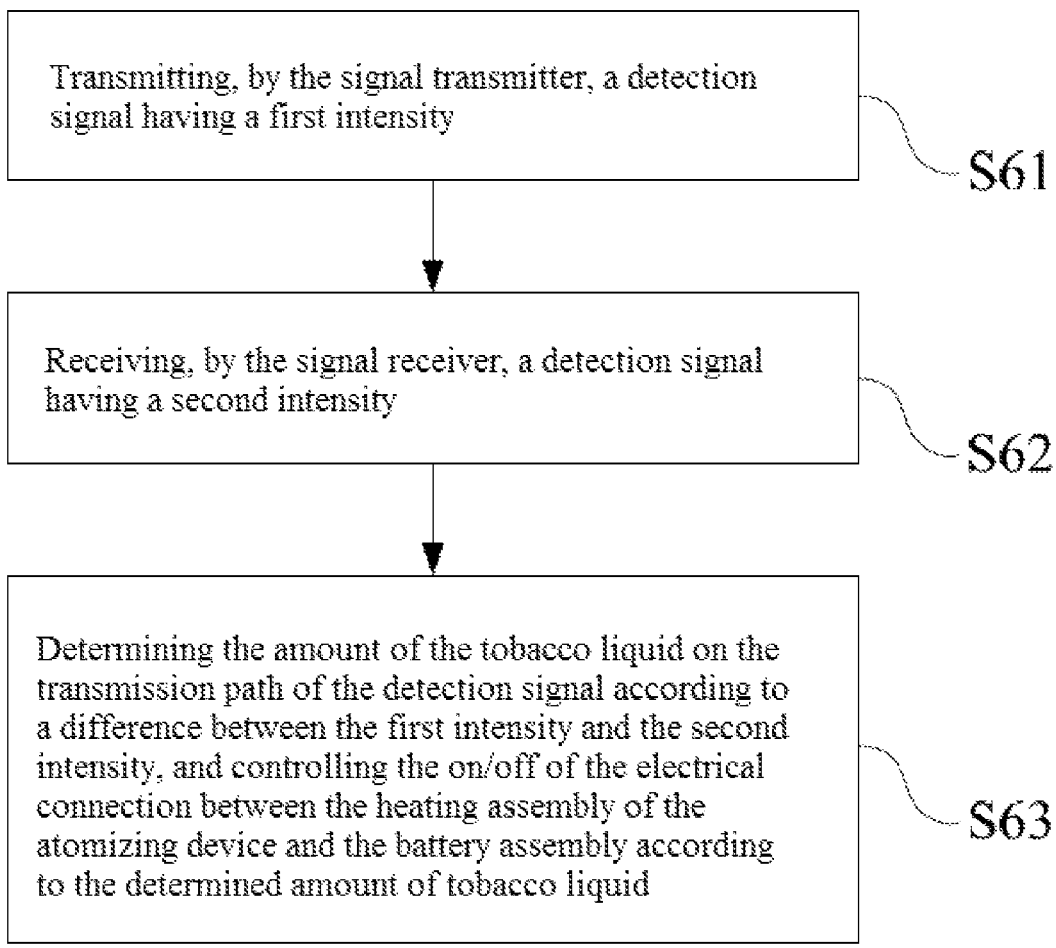
FIG. 6 is a flowchart of a control method for an atomizing device according to an embodiment of the present disclosure.

Referring to FIG. 6, which is a flowchart of an embodiment of a control method for an atomizing device provided by the present disclosure, the method includes the following steps:

S61: transmitting, by the signal transmitter, a detection signal having a first intensity.

S62: receiving, by the signal receiver, a detection signal having a second intensity.

S63: determining the amount of the tobacco liquid on the transmission path of the detection signal according to a difference between the first intensity and the second intensity, and controlling the on/off of the electrical connection between the heating assembly of the atomizing device and the battery assembly according to the determined amount of tobacco liquid.

Optionally, S63 can specifically be:
determining that the amount of the tobacco liquid on the transmission path of the detection signal is larger than a preset tobacco liquid amount value when the difference between the first intensity and the second intensity is greater than a preset difference value, and controlling the electrical connection between the heating assembly and the battery assembly to be ON; or,
determining that the amount of the tobacco liquid on the transmission path of the detection signal is less than a preset tobacco liquid amount value when the difference between the first intensity and the second intensity is less than a preset difference value, and controlling the electrical connection between the heating assembly and the battery assembly to be Off.

Optionally, in the above embodiments, the signal transmitter is an infrared signal transmitter, and the signal receiver is an infrared signal receiver; or, the signal transmitter is an ultrasonic signal transmitter, and the signal receiver is an ultrasonic signal receiver.

Optionally, in the above embodiments, the liquid guiding assembly is fiberglass; and/or the heating assembly is a heating wire.

It is understandable that the control method provided by the present embodiment is implemented based on the above atomizing device. The basic principles are similar, and no further description is needed here.

The above are embodiments of the present disclosure merely and are not intended to limit the patent scope of the present disclosure. Any equivalent structures or equivalent process transformation made according to the description and the accompanying drawings of the present disclosure, or any equivalent structures or equivalent flow modifications applied in other relevant technical fields directly or indirectly are intended to be included in the patent protection scope of the present disclosure.

What is claimed is:

1. An atomizing device, which is assembled with a battery assembly to form an electronic cigarette, comprising a liquid storage assembly configured for storing a tobacco liquid, a liquid guiding assembly connected to the liquid storage assembly and configured for guiding the tobacco liquid, and a heating assembly electrically connected to the battery assembly and configured for atomizing the tobacco liquid, wherein the atomizing device further comprises a signal transmitter and a signal receiver, the signal transmitter is configured for transmitting a detection signal having a first intensity of signal energy, and the signal receiver is configured for receiving a detection signal having a second intensity of signal energy; and the electronic cigarette is configured for determining an amount of the tobacco liquid on a transmission path of the detection signal according to a difference between the first intensity of signal energy and the second intensity of signal energy, and controlling the on/off of the electrical connection between the heating assembly and the battery assembly according to the determined amount of tobacco liquid;

wherein the signal transmitter is an infrared signal transmitter, and the signal receiver is an infrared signal receiver; or, the signal transmitter is an ultrasonic signal transmitter, and the signal receiver is an ultrasonic signal receiver;

wherein the atomizing device further comprises a controller configured for determining the amount of the tobacco liquid on the transmission path of the detection signal according to a difference between the first intensity of signal energy and the second intensity of signal energy and controlling on/off of the electrical connection between the heating assembly and the battery assembly according to the determined amount of tobacco liquid;

wherein the controller is specifically configured for determining that the amount of the tobacco liquid on the transmission path of the detection signal is larger than a preset tobacco liquid amount value when the difference between the first intensity of signal energy and the second intensity of signal energy is greater than a reset difference value, and controlling the electrical connection between the heating assembly and the battery assembly to be ON; and determining that the amount of the tobacco liquid on the transmission path of the detection signal is less than a reset tobacco liquid amount value when the difference between the first intensity of signal energy and the second intensity of signal energy is less than a preset difference value, and controlling the electrical connection between the heating assembly and the battery assembly to be OFF.

2. The atomizing device according to claim 1, wherein the liquid storage assembly is a hollow tubular structure; the signal transmitter and the signal receiver are arranged at two opposing sides of a bottom part of the hollow tubular structure respectively; or, the signal transmitter and the signal receiver are arranged at a top end and a bottom end of the hollow tubular structure respectively.

3. The atomizing device according to claim 2, wherein the hollow tubular structure has a through hole defined on a top part thereof, and the liquid guiding assembly is arranged in the through hole and extends into the inside and outside of the tubular structure so as to guide out the tobacco liquid in the liquid storage assembly.

4. The atomizing device according to claim 1, wherein the liquid guiding assembly is fiberglass; and/or the heating assembly is a heating wire.

5. An electronic cigarette, comprising a battery assembly and an atomizing device connected to the battery assembly, wherein the atomizing device is the atomizing device according to claim 1.

6. A control method for an atomizing device, comprising the steps of:
- transmitting, by a signal transmitter, a detection signal having a first intensity of signal energy;
- receiving, by a signal receiver, a detection signal having a second intensity, signal energy; and
- determining an amount of tobacco liquid on a transmission path of the detection signal according to a difference between the first intensity of signal energy and the second intensity of signal energy, and controlling on/off of electrical connection between the heating assembly of the atomizing device and the battery assembly according to the determined amount of tobacco liquid; wherein
- the signal transmitter is an infrared signal transmitter, and the signal receiver is an infrared signal receiver; or,
- the signal transmitter is an ultrasonic signal transmitter, and the signal receiver is an ultrasonic signal receiver, wherein a step of determining the amount of the tobacco liquid on the transmission path of the detection signal according to the difference between the first intensity of signal energy and the second intensity of signal energy, and controlling the on/off of the electrical connection between the heating assembly of the atomizing device and the battery assembly according to the determined amount of tobacco liquid comprises;

- determining that the amount of the tobacco liquid on the transmission path of the detection signal is larger than a preset tobacco liquid amount value when the difference between the first intensity a of signal energy and the second intensity of signal energy is greater than a preset difference value, and controlling the electrical connection between the heating assembly and the battery assembly to be ON; or
- determining that the amount of the tobacco liquid on the transmission path of the detection signal is less than a preset tobacco liquid amount value when the difference between the first intensity of signal energy and the second intensity of signal energy is less than a preset difference value, and controlling the electrical connection between the heating assembly and the battery assembly to be Off.

* * * * *